(12) United States Patent
Nordt

(10) Patent No.: US 7,731,719 B2
(45) Date of Patent: Jun. 8, 2010

(54) SAFETY KNIFE FOR RESECTION OF ANNULUS

(76) Inventor: John Nordt, 3580 Royal Palm Ave., Miami, FL (US) 33133-6225

( * ) Notice: Subject to any disclaimer, the term of this patent is extended or adjusted under 35 U.S.C. 154(b) by 1262 days.

(21) Appl. No.: 11/022,511

(22) Filed: Dec. 22, 2004

(65) Prior Publication Data

US 2006/0149267 A1 Jul. 6, 2006

(51) Int. Cl.
*A61B 17/00* (2006.01)
(52) U.S. Cl. .......................... 606/79; 606/83
(58) Field of Classification Search .............. 606/79, 606/83, 170; 30/27, 50, 78–80, 83, 346.57–346.59
See application file for complete search history.

(56) References Cited

U.S. PATENT DOCUMENTS

| | | | | |
|---|---|---|---|---|
| 2,029,495 | A | * | 2/1936 | Lowe ........................... 606/83 |
| 3,221,744 | A | * | 12/1965 | Stryker ........................ 606/83 |
| 3,452,754 | A | * | 7/1969 | Stayer ......................... 606/167 |
| 4,067,340 | A | | 1/1978 | LeNoir |
| 4,239,045 | A | * | 12/1980 | Schlein ........................ 606/83 |
| 4,678,459 | A | | 7/1987 | Onik et al. |
| 4,929,241 | A | * | 5/1990 | Kulli ........................... 604/263 |
| RE33,258 | E | | 7/1990 | Onik et al. |
| 5,055,106 | A | * | 10/1991 | Lundgren .................... 606/167 |
| 5,234,436 | A | * | 8/1993 | Eaton et al. ................. 606/107 |
| 5,254,128 | A | * | 10/1993 | Mesa ........................... 606/167 |
| 5,322,505 | A | | 6/1994 | Krause et al. |
| 5,391,169 | A | * | 2/1995 | McGuire ...................... 606/79 |
| 5,423,842 | A | | 6/1995 | Michelson |
| 5,649,945 | A | | 7/1997 | Ray et al. |
| 5,911,701 | A | * | 6/1999 | Miller et al. .................. 604/22 |
| 5,931,847 | A | * | 8/1999 | Bittner et al. ............... 606/167 |
| 6,200,322 | B1 | | 3/2001 | Branch et al. |
| 6,228,022 | B1 | | 5/2001 | Friesem et al. |
| 6,524,318 | B1 | | 2/2003 | Longhini et al. |
| 6,599,291 | B1 | | 7/2003 | Foley et al. |
| 6,689,132 | B2 | | 2/2004 | Biscup |
| 2003/0176881 | A1 | * | 9/2003 | Barlev ......................... 606/170 |

OTHER PUBLICATIONS

"Instruments for Knee Surgery," www.orthopaedic-implants.com, printed Jul. 21, 2004.

* cited by examiner

*Primary Examiner*—Nicholas D Lucchesi
*Assistant Examiner*—Julianna N. Harvey
(74) *Attorney, Agent, or Firm*—RatnerPrestia

(57) ABSTRACT

A cutting instrument for use in the complete removal of the annulus fibrosus of an intervertebral disc contains a curvature in the shaft. The curvature forms a guide that rests upon an intervertebral disc and guides the cutting head around the circumference of the intervertebral disc. The curvature of the shaft of the instrument conforms to the circumference of the intervertebral disc and prevents vessels and extra spinal tissue surrounding the intervertebral disc from being damaged particularly when cutting the posterior portion of the intervertebral disc where visibility is minimal. The cutting instruments contain blunt blade guards further minimizing any potential damage to tissue surrounding the intervertebral disc.

18 Claims, 7 Drawing Sheets

SAFETY KNIFE FOR RESECTION OF ANNULUS

FIELD OF INVENTION

This invention relates generally to the field of spinal surgery, particularly the complete anterior removal of the annulus fibrosus of the intervertebral disc, commonly performed during a discectomy when an artificial disc is being implanted. The invention comprises a cutting instrument that contains a curvature which conforms around the disc. The curvature of the shaft of the instrument forms a guide which rests upon the annulus fibrosus and intervertebral disc and guides the cutting head around the circumference of the intervertebral disc. The instrument conforms to the circumference of the intervertebral disc and prevents vessels and extra spinal tissue surrounding the intervertebral disc from being damaged particularly when cutting the posterior portion of the intervertebral disc where visibility is minimal. The cutting head of the instrument may contain single or dual cutting blades. The cutting instrument contains blunt blade guards further minimizing any potential damage to tissue surrounding the intervertebral disc.

BACKGROUND OF THE INVENTION

Intervertebral discs are found between the vertebral bodies which make up the spinal column. The intervertebral discs are fibrocartilaginous cushions that serve as spacers, shock absorbers and provide vertebral motion. The height of the disc maintains the distance of separation between the vertebral bodies, allowing for motion and room for spinal nerves to exit each spinal level with out being pinched or compressed. The disc serves as a shock absorber to protect the vertebrae, nerves and brain. The elasticity of the disc allows for vertebral motion. Intervertebral discs are composed of an annulus fibrosus and a nucleus pulposus. The annulus fibrosus encapsulates the inner nucleus pulposus portion of the disc. The annulus fibrosus is made up of concentric sheets of collagen fibers connected to the vertebral end plats. Both the annulus fibrosus and nucleus pulposus are composed of water, collagen and proteoglycans. Back pain is often caused by structural instability and dysfunction of the discs.

With the advent and increasing acceptance of artificial discs and the requirement for complete removal of an intervertebral disc or discectomy prior to insertion of an artificial disc, it will become increasingly important to be able to safely remove the entire intervertebral disc including the annulus fibrosus. Anterior discectomy is a dangerous procedure where the surgeon is operating very close to the spine and spinal tissue with instruments sharp enough to cut through the tough annulus fibrosus. Moreover, the disc is positioned between the vertebrae such that removal of the disc must be accomplished with minimal visibility when attempting to cut around the backside or posterior portion of the disc. The procedure of removing an entire disc will become a more frequent procedure, as replacement discs are now going through the approval process in the FDA and being introduced into the market.

Removal of the center portion, or nucleus pulposus, of the disc is known and has been used for several years to reduce back pain. Alternatively, fusion is used, which consists of removing portions of the problem disc and replacing it with a piece of bone taken from the patient's hip or a human cadaver. However, current surgical instrumentation, particularly, cutting instrumentation, are not adequate when performing complete removal of the disc, including removal of the annulus fibrosus of the disc. Currently available cutting instrumentation has a pointed sharp tip and can cause damage to vital blood vessels and the spinal tissue while removing the disc.

Several devices and instruments have been developed to be used in spinal surgery. U.S. Pat. No. 6,689,132 to Biscup (the '132 patent) discloses a spinal implant insertion tool. The tool facilitates in guiding and/or inserting one or more prosthetic implants into the intervertebral disc space. The insertion tool includes a body member and a curvilinear top portion connected to the body member. The top portion has a total angle of curvature of at least about 90% and a size and shape to enable over 50% of the top portion to be positioned within an outer perimeter of the intervertebral disc space. The tools can be provided in differently configured insertion tool set, which allows a surgeon to select the appropriate insertion tool that can be best used on a particular patient.

U.S. Pat. No. 6,599,291 to Foley et al. (the '291 patent) discloses methods and instruments for interbody surgical techniques, particularly methods and instruments for performing a surgical procedure in a disc space between adjacent vertebrae. The instruments include a distractor and a cutting instrument. The cutting instrument is positioned over the body portion and into the slots of the distractor so that the flanges are positioned between the cutting instrument and the adjacent tissue. This instrument provides for a number of cutters of increasing height to be used sequentially for removal of bony material from the vertebral endplates. Additionally, various shaped cutting edges can also be used, including flat cutting edges and rounded upper and lower cutting edges.

U.S. Pat. No. 6,228,022 to Friesem et al. (the '022 patent) discloses methods and instruments for spinal surgery, specifically, for preparing a disc space for implantation of a vertebral fusion or implant. The instrumentation includes a sleeve assembly with distraction fingers at one end to maintain distraction of a disc space. A switching sleeve having a pair of rotatable distractors is coupled within the outer sleeve, and the sleeves are placed over a dilator until the distractor heads are placed within the disc space. The dilator is withdrawn and the disc space distracted by rotating the distractors of the switching sleeve. The switching sleeve is uncoupled from the outer sleeve and the fingers of the outer sleeve are then inserted into the disc space. The switching sleeve and dilator are then removed and the outer sleeve defines a channel that allows insertion of implants at bilateral locations within the disc space without movement or manipulation of the outer sleeve.

U.S. Pat. No. 5,649,945 to Ray et al. (the '945 patent) discloses a spinal annulus cutter useful for cutting a multi-sided flap in an encapsulating ligament, such as an annulus of a disc, to provide access to an interior space. This instrument is not designed to be used in the removal of the entire disc, but rather is used in surgeries where the annulus is not removed. This surgical tool has the ability to pierce the annulus in such a way as to provide access to the discal area but allow for regenerative recover of the annular fibers afterwards, and prevent the damaging or destruction of the tightening or constraining ability of the annulus itself. The cutter is not designed to cut around the annulus.

U.S. Pat. No. 5,423,842 to Michelson (the '842 patent) discloses a spinal microknife. The knife was intended to simplify the procedure for performing an anterior cervical discectomy, while reducing the possibility of penetrating the dural sac or injuring the spinal cord. The microknife provides for an offset handle which allows unobstructed visualization of the cutting portion of the blade when operating on a cervical disc. The design of the blade tip has a smooth slightly biplanar convex bottom surface and a concave upper cutting surface, which will slip underneath the tissues to be cut, lifting the tissue onto the upper cutting portion of the blade which is perpendicular to the convex bottom surface. The tip of the knife is blunt to prevent puncturing. The knife is designed to allow for a safe way of cutting broadly across the posterior annulus or the posterior longitudinal ligament thus allowing full visualization of that space back there and the removal of any sequestered disc material under direct visualization.

U.S. Pat. No. 5,322,505 to Krause et al. (the '505 patent) discloses a powered arthroscopic surgical instrument, which includes a cutting implement disposed on the distal end of the inner tube. A region of the inner tube is flexible to enable the inner tube to accept the curvature imposed by the outer tube. The flexibility of the instrument allows the cutting tip to be manipulated into regions of the joint that cannot be reached by a straight instrument inserted through the same puncture.

U.S. Pat. No. 4,067,340 to LeNoir (the '340 patent) discloses a surgical instrument for meniscectomy. The instrument contains a pair of curved grooved guides of a shape corresponding to the periphery of the relatively inaccessible posterior portion of the meniscus. The cutting blade frame extends along the length of the grooved blade guide handles to the base of the two grooved guides and continues upward after being bent through an angle of approximately 100° with the cutting blade base mount. In operation, the flexible cutting blade advances along the grooves in the curved grooved guides and detaches the periphery of the meniscus near its base intra-articularly along a curved path corresponding to the shape of said curved grooved guides. This instrument is intended to replace both the Smillie and Lowe-Breck knives. The Smillie knives are a series of knives containing various angles which are used to perform a meniscectomy procedure on the knee.

One of the problems associated with the current surgical instruments that are used in the discectomy procedure is that they do not provide for the protection of other tissue structures near the intervertebral disc when the disc is being removed. Due to the great care that must be used in preventing any injury to tissue surrounding the intervertebral disc, such as the spinal cord, spinal tissue, nerve roots and iliac arteries and veins, safer cutting instruments are needed.

Additionally, there is a need for a surgical instrument that assists a surgeon in performing a discectomy, and specifically removing the annulus fibrosus, by following the curvature of the intervertebral disc as a guide. Such a cutting instrument would safely cut around the posterior portion of the disc where visibility is minimal, thus preventing injury to tissue surrounding the intervertebral disc. There is also a need for instruments that contains blunt blade guards to further prevent injury to surrounding tissue during the discectomy procedure and complete removal of the annulus fibrosus.

Alternatively, there is a need in the art for a set of cutting instruments for use in a discectomy procedure which when used sequentially, will safely cut around the tough annulus fibrosus of the intervertebral disc. Such instruments contain various curvatures that conform to various points around the circumference of the intervertebral disc.

SUMMARY OF THE INVENTION

The present invention solves significant problems in the art by providing instrumentation to be used in spinal surgery, specifically cutting instrumentation used to remove the annulus of the intervertebral disc to prepare the disc space for prosthetic placement. The invention consists of a cutting instrument that contains a curvature of the shaft which conforms to the circumference of the disc and uses the disc as a cutting guide. The cutting instrument contains blunt blade guards and the shaft of the instrument is curved to act as a guide so that the surgeon can follow the shape of the annulus fibrosus and disc around to the backside of the disc. The cutting head of the instrument may contain single or dual blades. The dual blades simultaneously cut both sides of the annulus, guided inside the annulus by the inferior blunt blade guard. Currently available cutting instruments do not allow for adequate control when cuts are made to the backside or posterior portion of the disc, where visibility is minimal. The curvature of the shaft of the instrument of the invention allows for the surgeon to be able to control the cuts around the disc, even on the backside of the disc. The cutting instrument cuts the annulus around the intervertebral disc, so that the instrument conforms to the circumference of the intervertebral disc and prevents tissue surrounding the intervertebral disc from being damaged, particularly when cutting the posterior portion of the intervertebral disc where visibility is minimal.

It is the object of the invention to provide a cutting instrument useful in removing the annulus fibrosus wherein the instrument comprises a cutting head, and wherein the cutting head consists of blunt blade guards and at least one blade. The blunt blade guards surround the blade or blades with a superior blade guard and an inferior blade guard. The shaft contains a curvature and connects to the cutting head. The curvature forms a guide which rests upon an intervertebral disc and guides the cutting head around the circumference of the intervertebral disc and annulus fibrosus. The shaft of the instrument is designed ergonomically to allow continuous cutting from about 45 degrees off of the center of the disc to the posterior annulus.

It is yet another object of the invention to provide a cutting instrument comprising a shaft having a proximal end and a distal end. The cutting head attaches to the distal end of the shaft. The cutting head is formed from at least two blunt blade guards and at least one blade, wherein the shaft is curved so that said cutting head closely conforms to a circumference of a portion of an intervertebral disc. Also disclosed is a safety knife useful for safely removing an annulus fibrosus of an intervertebral disc comprising a cutting head, wherein the cutting head contains at least two blunt blade guards and at least one blade. The shaft of the cutting instrument contains a curvature to closely conform a circumference of an intervertebral disc.

In another embodiment of the invention provided are a series of cutting instruments useful in resection of an annulus fibrosus wherein the series of instruments consists of at least two instruments, each instrument comprising a cutting head, wherein the cutting head consists of blunt blade guards and at least one blade. The blunt blade guards surround the blade with a superior blade guard and an inferior blade guard. The cutting instruments also contain a shaft, wherein the shaft contains a curvature. The curvature of the shaft forms a guide which rests upon an intervertebral disc and guides the cutting head around the circumference of the intervertebral disc. The curvature of the shafts are varied between each instrument in the series such that each instrument is sequentially used to cut around the circumference of the intervertebral disc.

DETAILED DESCRIPTION OF THE PREFERRED EMBODIMENT

Figure 1:
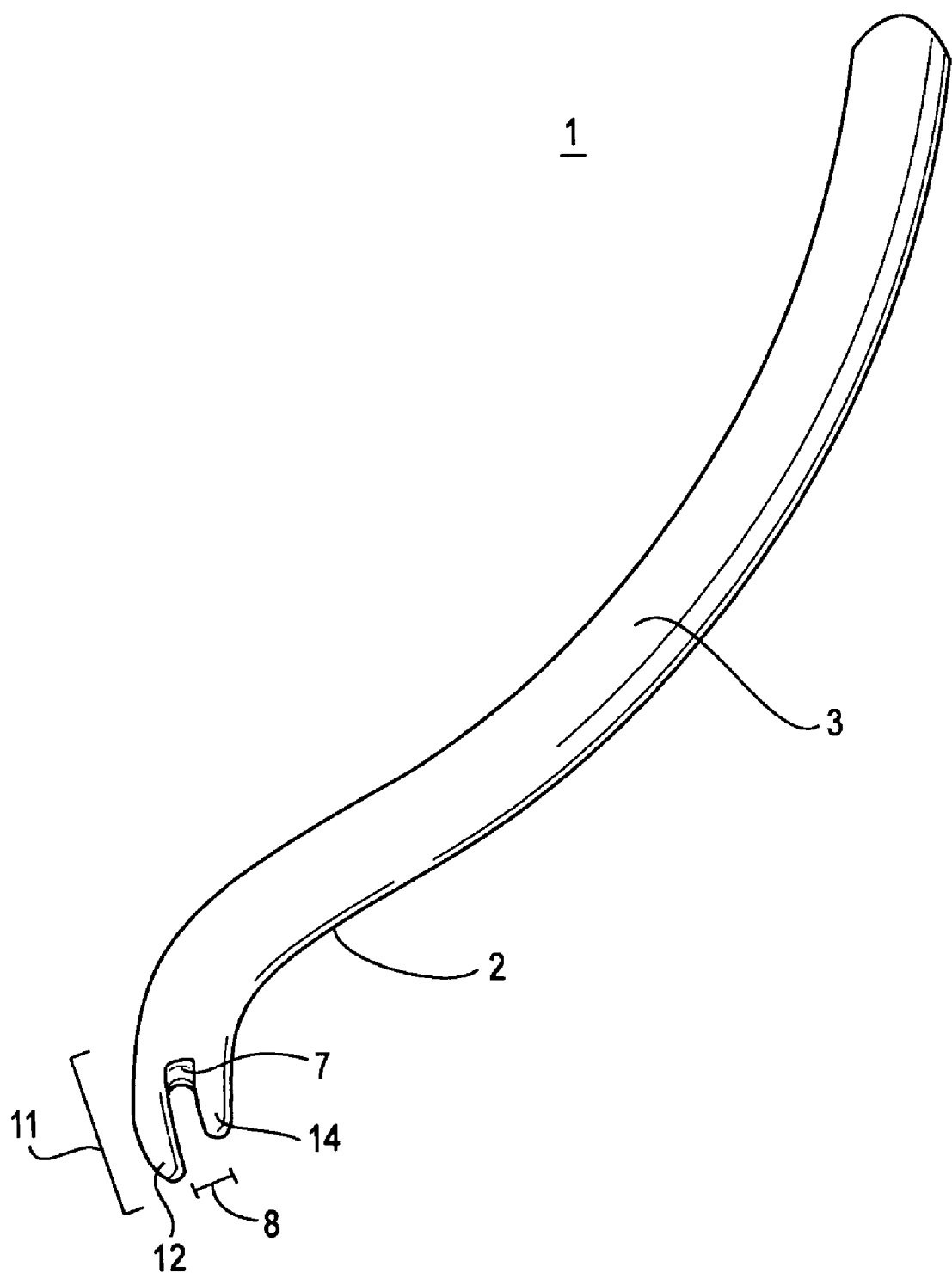
FIG. 1 is a side view of a cutting instrument showing the curvature of the instrument.

While the invention is susceptible of several embodiments, there is shown in the drawings, specific embodiments thereof, with the understanding that the present disclosure is to be considered as an exemplification of the invention and is not intended to limit the invention to the specific embodiments shown.

Referring initially to FIG. 1 of the drawings, in which like numerals indicate like elements throughout the several views, shown is the side view of a cutting instrument 1. The curvature 2 of the shaft 3 of the instrument demonstrates the ability of the cutting instrument 1 to follow the circumference around the intervertebral disc while the annulus fibrosus is being resected. The instrument contains a curvature 2 of the shaft 3 just before the cutting head 4. The preferred embodiment contains a dual bladed cutting head 4; however, a single bladed cutting head 4 could be used.

The instrument consists of a handle or a shaft 3. The shaft 3 connects to a cutting head 4 comprised of blunt blade guards 12 and 14 which hold a blade 7. The width 8 between the blunt blade guards 12 and 14 can be varied to fit the different thicknesses of the annulus fibrosus of the intervertebral disc. The width 8 between the blunt blade guards 12 and 14 may be varied from approximately 6 mm to 12 mm. The width 8 may be varied between consecutive instruments or alternatively include a mechanism to adjust the width 8 on the instrument. The blunt blade guards consist of a superior guard 12 and an inferior guard 14. These blunt blade guards 12 and 14 function to prevent unwanted nicks or cuts to tissue surrounding the intervertebral disc. The cutting head 4 is attached to the shaft 3 at a curvature 2.

Figure 2:
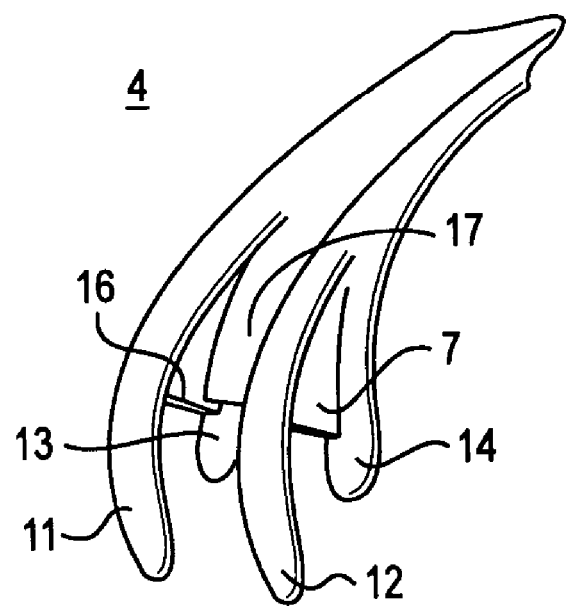
FIG. 2 is a front isometric view of the cutting head of the instrument.

FIG. 2 shows a front view of the cutting head 4 of the instrument. The instrument is shown as a dual bladed instrument. The cutting head includes a right superior blunt blade guard 11, a left superior blunt blade guard 12, a right inferior blunt blade guard 13, and a left inferior blunt blade guard 14. The width between the right superior blunt blade guard 11 and the left superior blunt blade guard 12 is approximately 8 mm to 15 mm. This width may be adjustable or optionally, it may be varied between consecutive instruments. Between the right superior blunt blade guard 11 and the right inferior blunt blade guard 13 lies a cutting edge or blade 16. Between the left superior blunt blade guard 12 and the left inferior blunt blade guard 14 lies a cutting edge or blade 7. This dual bladed cutting head 4 dissects the annulus fibrosus simultaneously on both sides of the annulus fibrosus where it is connected to the vertebrae. As the annulus fibrosus is cut and removed, the resected portion flows up over the top of the instrument between the right superior blunt blade guard 11 and a left superior blunt blade guard 12 onto a ramp 17. The ramp 17 has a general incline until it meets the shaft of the instrument. The ramp 17 directs the cut annulus fibrosus away from the surgical site. The leading edge of ramp 17 may be sharp or dull. If the leading edge of the ramp 17 is sharp, it will function like a blade and work in conjunction with the other blades. This would form a three sided blade.

Figure 3:
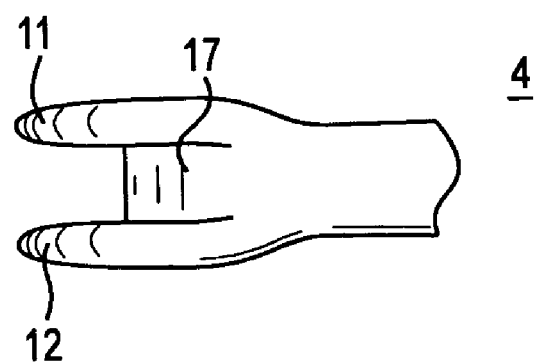
FIG. 3 is a top view of the cutting head of the instrument.
Figure 4:
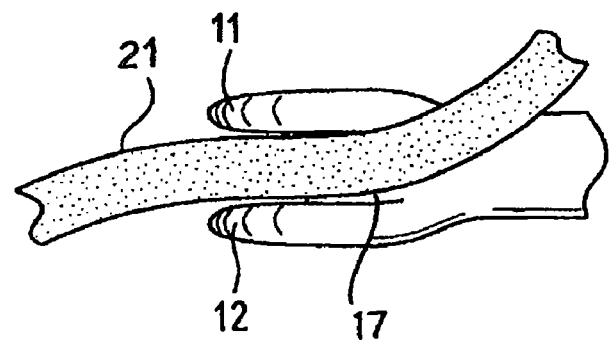
FIG. 4 is a top view of the cutting head of the instrument actually cutting the annulus fibrosus.

FIG. 3 and FIG. 4 are top views of the cutting head 4 of the instrument. The right superior blunt blade guard 11 and the left superior blunt blade guard 12 are shown on either side of the ramp 17. The ramp 17 provides a connection between the left and right superior blunt blade guards 11 and 12, which provides strength and support to the superior blunt blade guards 11 and 12. The ramp 17 gradually inclines to meet the shaft 3 of the instrument 1. The gradual incline of the ramp 17 serves to direct and guide the cut annulus fibrosus 21 away from the cutting head 4. In FIG. 4, the annulus fibrosus 21 is shown as it is dissected and falls away from the surgical site as directed from the ramp 17.

Figure 5:
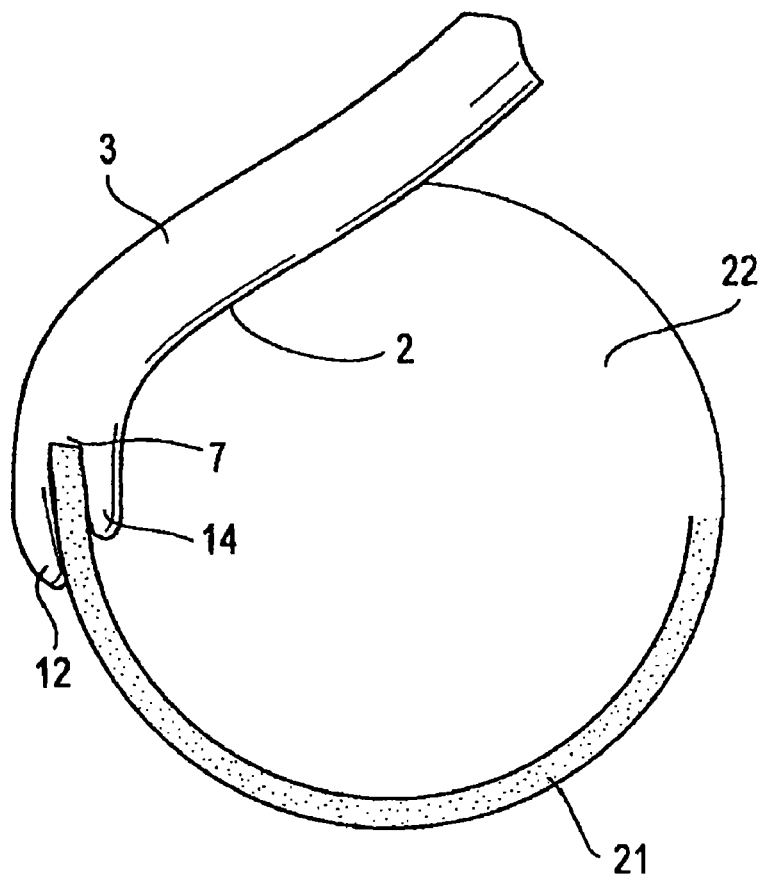
FIG. 5 is a side view of the cutting instrument showing the placement of the superior and inferior blunt blade guards around the annulus fibrosus.

FIG. 5 is a side view of the cutting instrument showing the placement of the superior 12 and inferior 14 blunt blade guards around the annulus fibrosus 21. The curvature 2 of the shaft 3 of the cutting instrument 1 follows the circumference of the intervertebral disc 22 while the annulus fibrosus 21 is resected. The inferior blunt blade guard 14 lies underneath the annulus fibrosus 21 while the superior blunt blade guard 12 follows the surface of the annulus fibrosus 21. Both of the blunt blade guards 12 and 14 act to catch the annulus fibrosus 21 between the superior and inferior blunt blade guards 12 and 14, while at the same time directing the annulus fibrosus 21 up into the blade 7. The curvature 2 of the instrument prevents the cutting instrument 1 from lacerating structures not intended to be cut. This is especially crucial around the side and backside or posterior portion of the intervertebral disc 22 where the spinal tissue lies. The blunt blade guards 12 and 14 of the instrument also prevent structures surrounding the intervertebral disc 22 from being inadvertently damaged by the blades 7 and 16 of the cutting instrument 1. Referring back to FIG. 2, when a dual cutting head is employed, blunt blade guards 11 and 13 also serve to catch the annulus fibrosus 21 between the superior and inferior blunt blade guards 11 and 13, while at the same time directing the annulus fibrosus 21 up into the blade 16.

Figure 6:
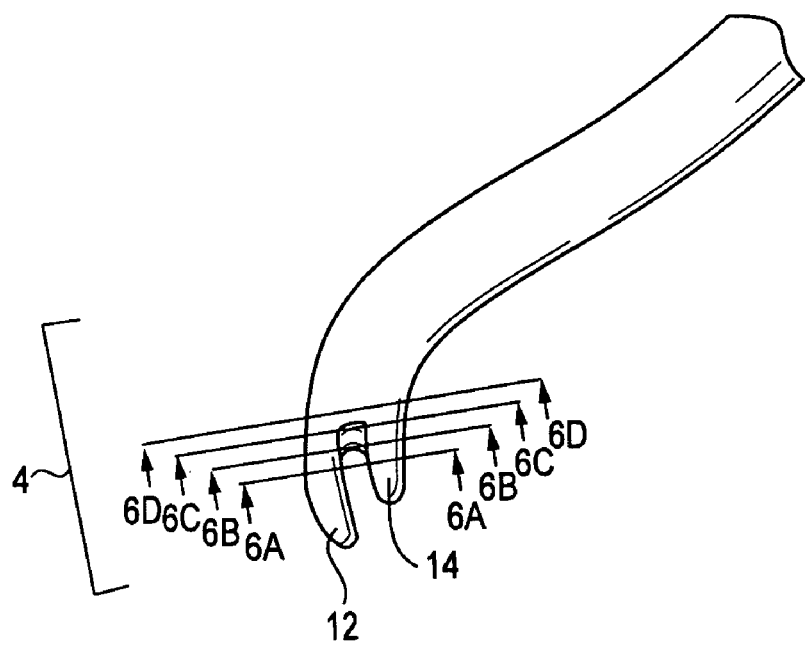
FIG. 6 is a side view of the instrument and correlating cross-sectional views at various points.
Figure 6A:
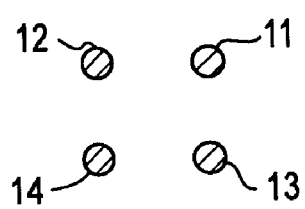
Figure 6B:
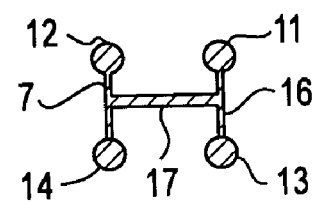
Figure 6C:
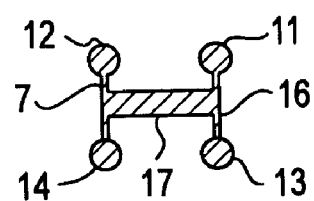
Figure 6D:
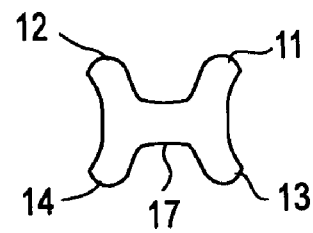

Now referring to FIG. 6 shown is a side view of a dual bladed cutting head 4 of the cutting instrument 1 along with cross-sectional views of various portions of the cutting head 4. View A represents a cross section through a first portion of the cutting head 4. As can be seen, the superior blunt blade guards 12 and 11 and inferior blunt blade guards 14 and 13 serve to protect surrounding tissue and direct the annulus fibrosus to the cutting blades 7 and 16. View B represents a cross section through a middle portion of the cutting head 4. Shown are the superior blunt blade guards 12 and 11 and inferior blunt blade guards 14 and 13. Extending vertically between superior blunt blade guard 12 and inferior blunt blade guard 14 is blade 7. Extending vertically between superior blunt blade guard 11 and inferior blunt blade guard 13 is blade 16. Also shown in View B is the beginning portion of ramp 17. View C is another cross section of the middle of the cutting head 4, further toward the shaft of the cutting instrument. The same portions of the cutting head shown in View B are again shown in View C. As can be seen, the ramp 17 increases in thickness as the incline of the ramp increases toward the shaft of the instrument. View D is a cross section of the last portion of the cutting head nearest to the shaft of the instrument. The connection of the superior and inferior blunt blade guards 12, 11, 14 and 13 can be seen. Additionally, the increasing thickness of the ramp 17 is shown. The ramp 17 is the cross piece that connects the blunt blade guards 12 and 14 with the blunt blade guards 11 and 13 and serves to strengthen the instrument and eventually blends into the shaft.

Figure 7:
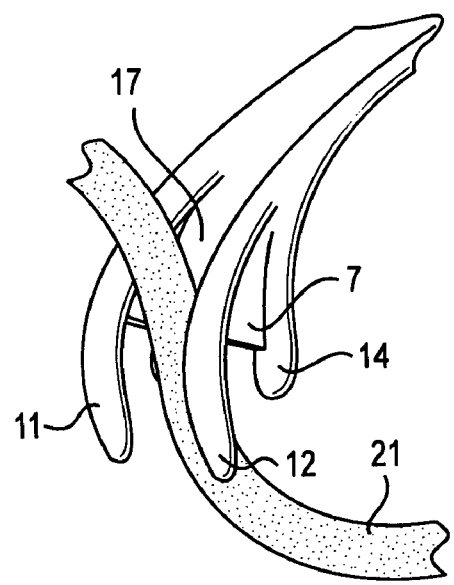
FIG. 7 is a side isometric view of a dual blade cutting head resecting the annulus fibrosus.
Figure 8:
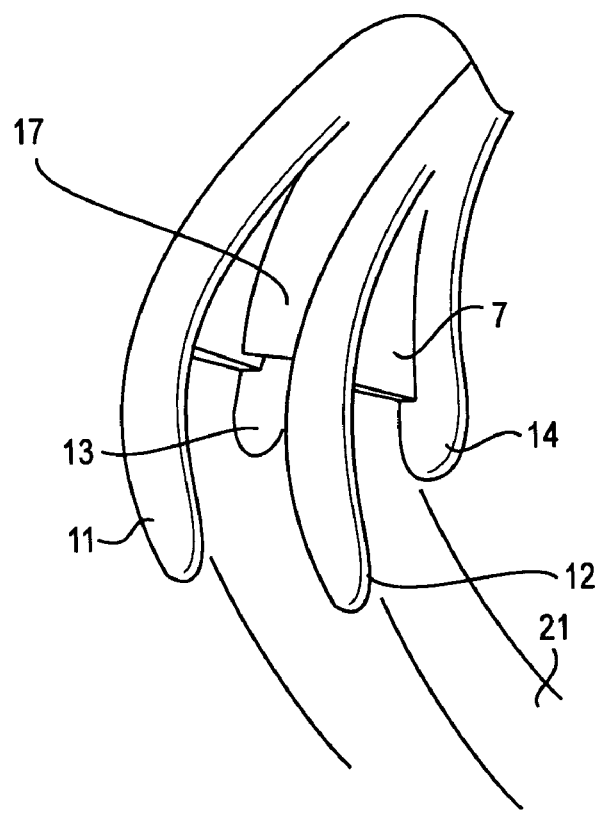
FIG. 8 is a frontal isometric view close up of a dual blade cutting head resecting the annulus fibrosus.
Figure 9:
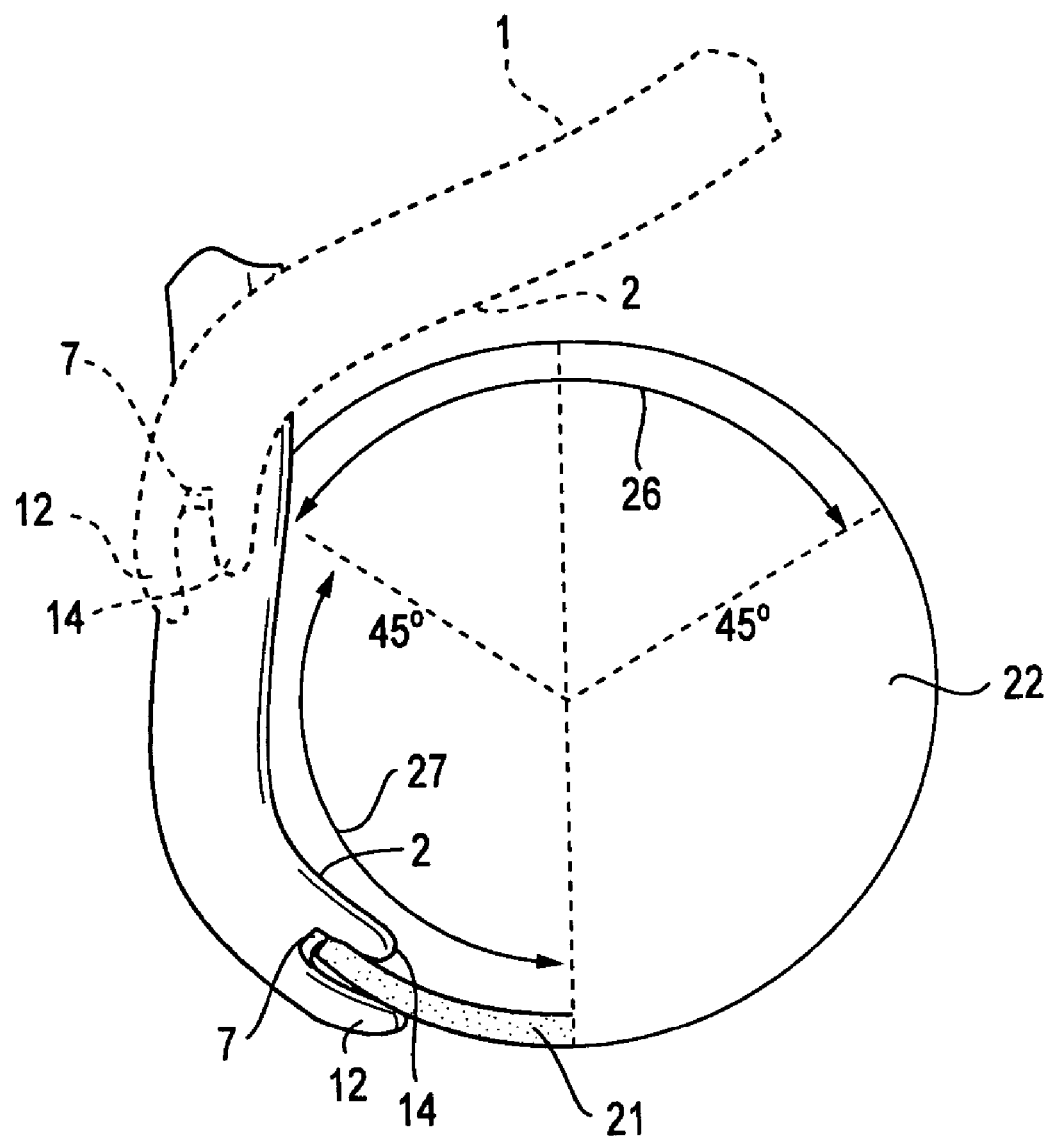
FIG. 9 is an axial view of an intervertebral disc showing the various positions of the instrument around the disc.

FIG. 7 is a view from the top and side of a dual blade cutting head 4 resecting the annulus fibrosus 21. FIG. 8 is another frontal view close-up of a dual blade cutting head 4 resecting the annulus fibrosus 21. Both of these figures show the interaction of the superior and inferior blunt blade guards 11, 12, 13 and 14 and the annulus fibrosus 21. FIG. 9 is an axial view of an intervertebral disc showing the various positions of the instrument around the disc. Two instruments are shown simultaneously in the drawing, but it is understood that the instrument is used to continuously cut around the annulus fibrosus. Typically the portion of the annulus fibrosus 21 within arc 26 may be opened and removed with a sharp blade prior to using the cutting instrument 1, because this portion is clearly visible from the surgical opening in the abdomen of the patient. The cutting instrument 1 may then be used to remove the annulus fibrosus 21 within arc 27 on either side of arc 26. The portion of the annulus fibrosus 21 within arc 27 is more difficult to reach and less visible from the surgical site. The use of the cutting instrument 1 allows the surgeon to safely cut around the annulus fibrosus 21 of the intervertebral disc 22 where visibility is minimal. Flanked on either side of the intervertebral disc 22 typically are the left common iliac vein and the right common iliac artery. Directly behind the site of surgery that is used to access the intervertebral disc 22 is the spinal tissue. Great care must be taken to avoid injury to the vascular and nervous system, especially the spinal tissue.

During a surgical discectomy to prepare the disc space for an artificial disc, complete removal of the disc 22, including the inner nucleus pulposus and annulus fibrosus 21 is typically required. The complete disc 22 removal may be accomplished by first opening the annulus fibrosus 21 with a regular surgical sharp blade along arc 26. Then, the inner nucleus pulposus may be removed from the inside of the disc 22 space. Once the nucleus pulposus is removed, the annulus fibrosus 21 can be completely removed along arc 27 on either side of arc 26, with the cutting instrument 1. When using a single blade cutting instrument, the superior blunt blade guard 12 approximates the circumference and curvature of the annulus fibrosus 21 while the inferior blunt blade guard 14 lies inside and is guided by the annulus fibrosus 21. Referring back to FIG. 2, when using a dual bladed cutting instrument, the superior blunt blade guards 12 and 11 approximate the circumference and curvature of the annulus fibrosus while the inferior blunt blade guards 14 and 13 lie inside and are guided by the annulus fibrosus 21. The blades 7 and 16 on either side of a dual bladed cutting head 4 cut the annulus fibrosus 21 simultaneously. Once cut, the annulus fibrosus 21 slides off of the top of the ramp 17 of the instrument 1.

Referring back to FIGS. 1 and 2, the various components of the cutting instrument 1 shall be described in detail. The blades 7 and 16 of the instrument may be disposable, replaceable, interchangeable, serrated, a straight sharp blade (as shown in FIG. 2, for example) or contain teeth. The instrument 1, including the shaft 3 and cutting head 4 may be entirely disposable or reusable. The instrument 1 may be made of plastic, metal, carbon fiber or other suitable materials. The shaft 3 of the instrument can be made to be flexible to allow for a slight bending of the curvatures 2 of the instruments so that each instrument more closely conforms to the circumference of the disc when pressure is applied to the instrument.

In an alternate embodiment, the shaft 3 may be contain a pivoting hinge which allows the instrument to bend respective to the shaft 3 and cutting head 4. Such a pivoting hinge would have a maximum and minimum bending stop point, which would prevent it from pivoting beyond those limits. In yet another embodiment of a dual bladed cutting head 4, the two superior blunt blade guards 11 and 12 may be connected forming one large superior blunt blade guard. This large superior blunt blade guard would serve to prevent damage to structures surrounding the intervertebral disc.

Figure 10A:
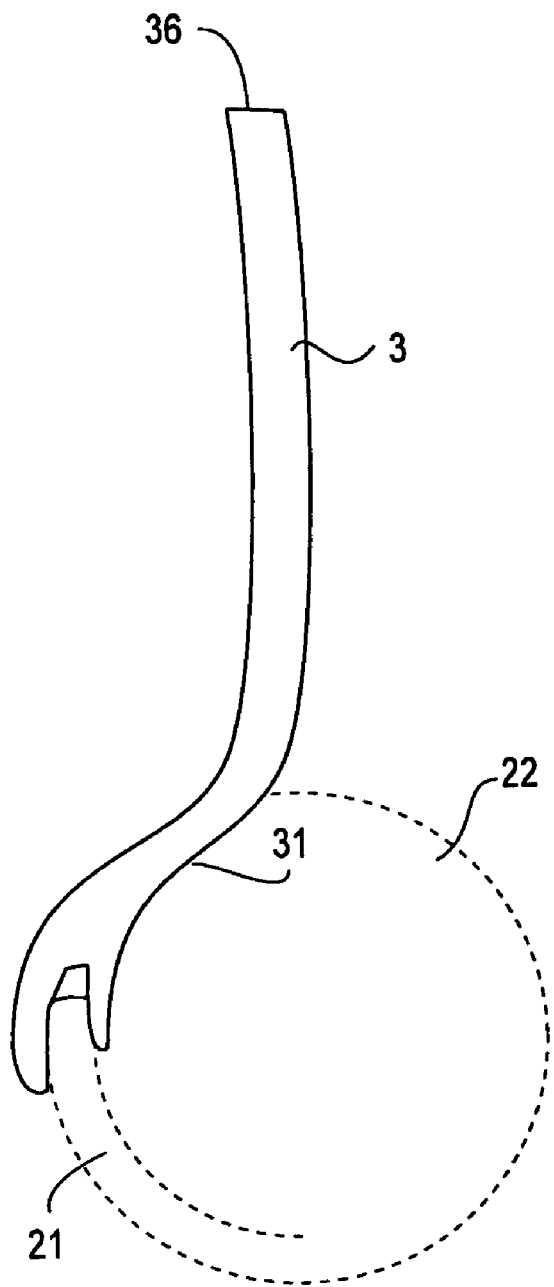
FIG. 10 is a side view of a series of cutting instruments.
Figure 10B:
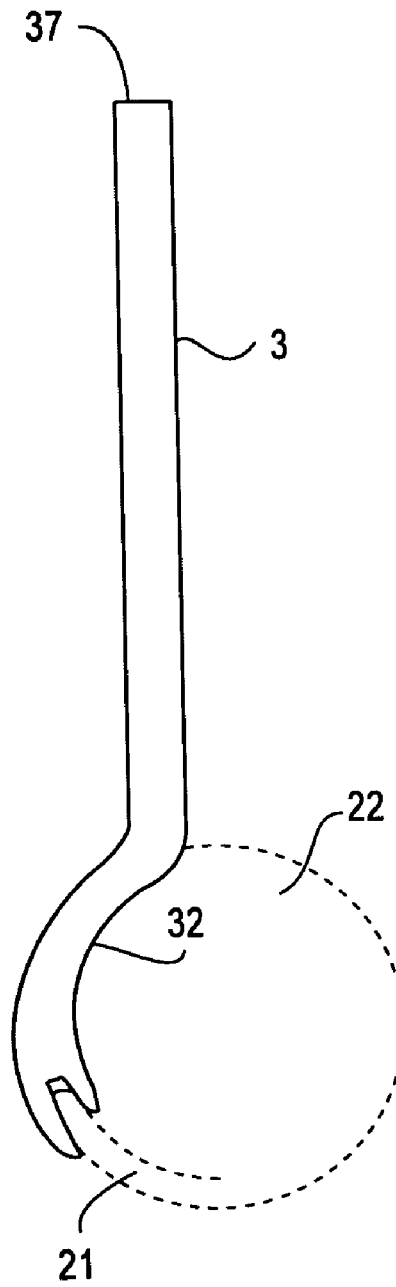

In an alternate embodiment, as shown in FIG. 10, the discectomy is performed using a series of instruments 34 sequentially to follow the circumference of the intervertebral disc 22 around the annulus fibrosus 21. The series of instruments 34 contain at least two instruments with an increase in the curvature 31 and 32 of the shaft 3 between each instrument. The increase in curvature 31 and 32 of each sequential instrument allows the surgeon to cut around the sides and posterior portion of the disc 22 where visibility is minimal. The curvature 31 and 32 of the cutting instruments act as a guide whereby the cutting instrument closely follows the circumference of the intervertebral disc 22 preventing damage to any other nearby tissue. For example, the first instrument 36 contains a minimal curvature 31 of the lowest portion of the shaft 3. The lowest portion of the shaft 3 of the next instrument 37 of the series contains a significant curve 32. This increase in curvature allows the instruments 34 to be used sequentially on differing portions of the circumference of the intervertebral disc 22. For example, as the surgeon begins to cut closer to the side and anterior portion of the annulus fibrosus 21 where visibility is minimal, the surgeon would use the instrument that most closely fits the curvature of that particular portion of the annulus fibrosus and intervertebral disc 22.

Accordingly, it will be understood that the preferred embodiment of the present invention has been disclosed by way of example and that other modifications and alterations may occur to those skilled in the art without departing from the scope and spirit of the appended claims.

What is claimed is:

1. An instrument for shaving annulus fibrosis of an intervertebral disc from vertebrae, the instrument comprising:
   a first shaving member extending in a distal direction for shaving annulus fibrosis from a first vertebral body;
   a second shaving member extending in the distal direction generally parallel to the first shaving member for shaving annulus fibrosis from a second vertebral body;
   a ramp extending transversely directly between midpoints of the first shaving member and the second shaving member; and
   a plurality of blunt guards extending distally beyond the first and second shaving members.

2. The instrument of claim 1, wherein the plurality of blunt guards comprises a first pair of blunt guards straddling the first shaving member and a second pair of blunt guards straddling the second shaving member.

3. The instrument of claim 2, wherein each pair of blunt blade guards includes a superior blunt blade guard and an inferior blunt blade guard.

4. The instrument of claim 3 wherein said superior blunt blade guard of each pair extends beyond said inferior blunt blade guard of each pair and prevents tissue surrounding the intervertebral disc from being damaged when cutting a posterior portion of the intervertebral disc.

5. The instrument of claim 3 wherein a width between said superior blunt blade guard and inferior blunt blade guard varies from about 6 mm to about 12 mm.

6. The instrument of claim 3 wherein a width between said superior blunt blade guards varies from about 8 mm to about 15 mm.

7. The instrument of claim 1, wherein the first and second shaving members and the ramp each have a distal edge, the distal edges collectively forming three sides of a rectangular blade.

8. The instrument of claim 1 further comprising a curved shaft extending in a proximal direction from the ramp.

9. The instrument of claim 8, wherein at least a portion of the ramp includes a curvature matching a curvature of the curved shaft.

10. The instrument of claim 8, wherein the ramp increases in thickness in the proximal direction towards the shaft.

11. The instrument of claim 1 wherein said shaving members are replaceable or interchangeable.

12. The instrument of claim 1 wherein said instrument is made of metal.

13. The instrument of claim 1 wherein said instrument is made of carbon fiber.

14. The instrument of claim 1 wherein said instrument is disposable.

15. The instrument of claim 1 wherein each shaving member is a straight sharp blade.

16. An instrument for shaving and preserving annulus fibrosis of an intervertebral disc for subsequent use and repair of said annulus fibrosis in the same procedure, the instrument comprising:
   a first annulus shaver extending in a distal direction for shaving said annulus fibrosis from the surface of a first vertebra;
   a second annulus shaver extending in a distal direction generally parallel to the first annulus shaver for shaving said annulus fibrosis from the surface of a second vertebra; and an annulus resector extending transversely directly between midpoints of the first and second annulus shavers for resecting a portion of said annulus fibrosis, said resector forming a ramp for guiding resected portions of the annulus fibrosis in a preserved state still attached to the disc.

17. An instrument for shaving and preserving annulus fibrosis of an intervertebral disc for subsequent use and repair of said annulus fibrosis in the same procedure, the instrument comprising:
   a first annulus shaver extending in a distal direction for shaving said annulus fibrosis from the surface of a first vertebra;
   a second annulus shaver extending in a distal direction generally parallel to the first annulus shaver for shaving said annulus fibrosis from the surface of a second vertebra; and
   an annulus resector extending transversely between the first and second annulus shavers for resecting a portion of said annulus fibrosis, said resector forming a curved surface for guiding resected portions of the annulus fibrosis in a preserved state still attached to the disc,
   the first annulus shaver, second annulus shaver and resector each comprising a generally straight distal edge, the distal edges forming a three-sided box-shaped channel at the distal end of the instrument having first and second cutting planes generally parallel to one another, and a third cutting plane extending transversely between the first and second cutting planes.

18. The instrument of claim 17, wherein the distal edges of the first annulus shaver, second annulus shaver and resector form an H-shaped configuration.

\* \* \* \* \*